(12) United States Patent
Toth et al.

(10) Patent No.: US 6,310,938 B1
(45) Date of Patent: Oct. 30, 2001

(54) METHODS AND APPARATUS FOR CALIBRATING CT X-RAY BEAM TRACKING LOOP

(75) Inventors: Thomas L. Toth, Brookfield; George E. Seidenschnur, Waukesha; Neil B. Bromberg, Milwaukee, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/384,937

(22) Filed: Aug. 27, 1999

(51) Int. Cl.$^7$ .................................................. G21K 1/00
(52) U.S. Cl. ........................... 378/147; 378/4; 378/207; 378/151; 378/19
(58) Field of Search ............... 378/4, 207, 147, 378/151, 19, 113, 686

(56) References Cited

U.S. PATENT DOCUMENTS

| | | |
|---|---|---|
| 4,991,189 | 2/1991 | Boomgaarden et al. . |
| 5,299,250 | 3/1994 | Styrnol et al. . |
| 5,469,429 | 11/1995 | Yamazaki et al. . |
| 5,485,493 | 1/1996 | Heuscher et al. . |
| 5,550,886 | 8/1996 | Dobbs et al. . |
| 5,579,359 | 11/1996 | Toth . |
| 5,610,963 * | 3/1997 | Hsieh ........................................ 378/7 |
| 5,684,855 * | 11/1997 | Aradate et al. ........................... 378/4 |
| 5,745,548 | 4/1998 | Dobbs et al. . |
| 5,761,257 | 6/1998 | Toth et al. . |
| 6,056,437 * | 5/2000 | Toth ...................................... 378/205 |
| 6,115,447 * | 9/2000 | Hsieh ...................................... 378/19 |
| 6,141,402 * | 10/2000 | Toth ..................................... 378/150 |

FOREIGN PATENT DOCUMENTS

| | | |
|---|---|---|
| 19650528 | 12/1996 | (DE) . |
| WO00/30538 | 11/1999 | (WO) . |

OTHER PUBLICATIONS

U.S. application No. 08/576,066, Toth et al., filed Dec. 21, 1995.

U.S. application No. 09/199,170, Toth et al., filed Dec. 2, 1998.

U.S. application No. 09/384,169, Toth et al., filed Aug. 27, 1999.

* cited by examiner

Primary Examiner—Robert H. Kim
Assistant Examiner—Hoon K. Song
(74) Attorney, Agent, or Firm—Armstrong Teasdale LLP; Christian G. Cabou (57) ABSTRACT

The present invention is, in one embodiment, a method for determining tracking control parameters for positioning an x-ray beam of a computed tomography imaging system having a movable collimator positionable in steps and a detector array including a plurality of rows of detector elements. The method includes steps of obtaining detector samples at a series of collimator step positions while determining a position of a focal spot of the x-ray beam; determining a beam position for each detector element at each collimator step utilizing the determined focal spot positions, a nominal focal spot length, and geometric parameters of the x-ray beam, collimator, and detector array; and determining a calibration parameter utilizing information so obtained. For example, in determining a target beam position at which to maintain the x-ray beam, a detector element differential error is determined according to ratios of successive collimator step positions; and a target beam position is selected for an isocenter element in accordance with the determined element differential errors.

26 Claims, 4 Drawing Sheets

METHODS AND APPARATUS FOR CALIBRATING CT X-RAY BEAM TRACKING LOOP

BACKGROUND OF THE INVENTION

This invention relates generally to computed tomography (CT) imaging and, more particularly, to methods and apparatus for calibration of z-axis tracking loops for positioning a CT x-ray beam of a multi-slice CT imaging system.

In at least one known computed tomography (CT) imaging system configuration, an x-ray source projects a fan-shaped beam which is collimated to lie within an X-Y plane of a Cartesian coordinate system and generally referred to as the "imaging plane". The x-ray beam passes through the object being imaged, such as a patient. The beam, after being attenuated by the object, impinges upon an array of radiation detectors. The intensity of the attenuated beam radiation received at the detector array is dependent upon the attenuation of the x-ray beam by the object. Each detector element of the array produces a separate electrical signal that is a measurement of the beam attenuation at the detector location. The attenuation measurements from all the detectors are acquired separately to produce a transmission profile.

In known third generation CT systems, the x-ray source and the detector array are rotated with a gantry within the imaging plane and around the object to be imaged so that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector. In an axial scan, the projection data is processed to construct an image that corresponds to a two-dimensional slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display.

In a multi-slice system, movement of an x-ray beam penumbra over detector elements having dissimilar response functions can cause signal changes resulting in image artifacts. Opening system collimation to keep detector elements in the x-ray beam umbra can prevent artifacts but increases patient dosage. Known CT systems utilize a closed-loop z-axis tracking system to position the x-ray beam relative to a detector array. It would be desirable to provide improved methods and apparatus for calibration of such systems. In particular, it would be desirable to provide improved methods and apparatus for determining calibration parameters such as: (1) a target beam position at which to maintain the x-ray beam; (2) a transfer function to convert sensed tracking information into a beam position in millimeters; and (3) valid limits of the transfer function.

BRIEF SUMMARY OF THE INVENTION

There is therefore provided, in one embodiment, a method for determining tracking control parameters for positioning an x-ray beam of a computed tomography imaging system having a movable collimator positionable in steps and a detector array including a plurality of rows of detector elements. The method includes steps of obtaining detector samples at a plurality of collimator step positions while determining a position of a focal spot of the x-ray beam; determining a beam position for each detector element at each collimator step utilizing the determined focal spot positions, a nominal focal spot length, and geometric parameters of the x-ray beam, collimator, and detector array; and determining a calibration Parameter utilizing information so obtained. For example, in determining a target beam position at which to maintain the x-ray beam, the method also includes steps of determining an detector element differential error according to ratios of successive collimator step positions; and selecting a target beam position for an isocenter element in accordance with the determined element differential errors.

The above described system provides improved tracking calibration for CT imaging systems utilizing z-axis tracking loops for positioning x-ray beams.

DETAILED DESCRIPTION OF THE INVENTION

Figure 1:
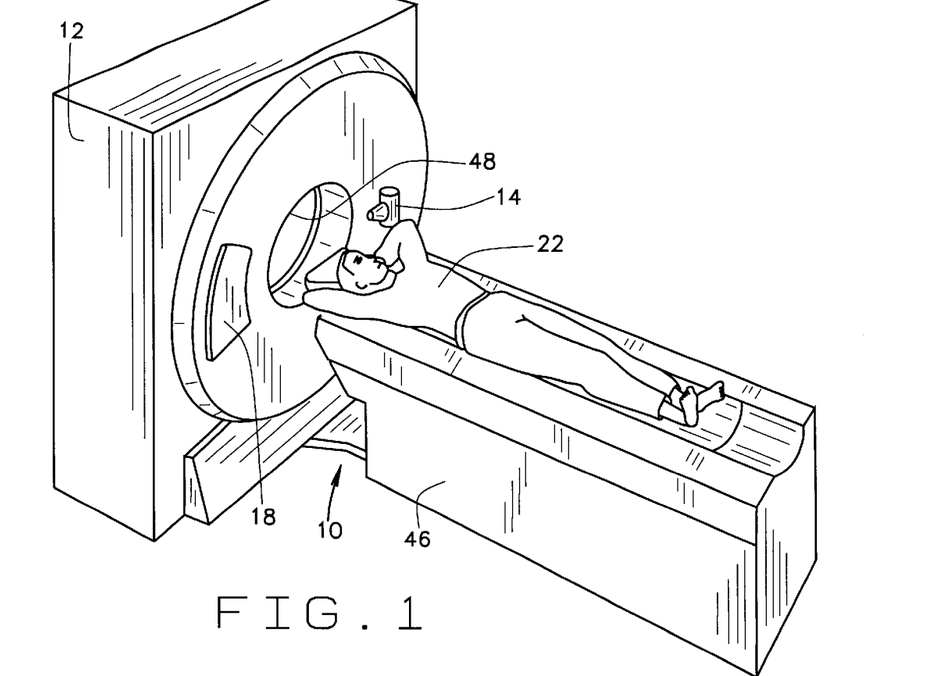
FIG. 1 is a pictorial view of a CT imaging system.
Figure 2:
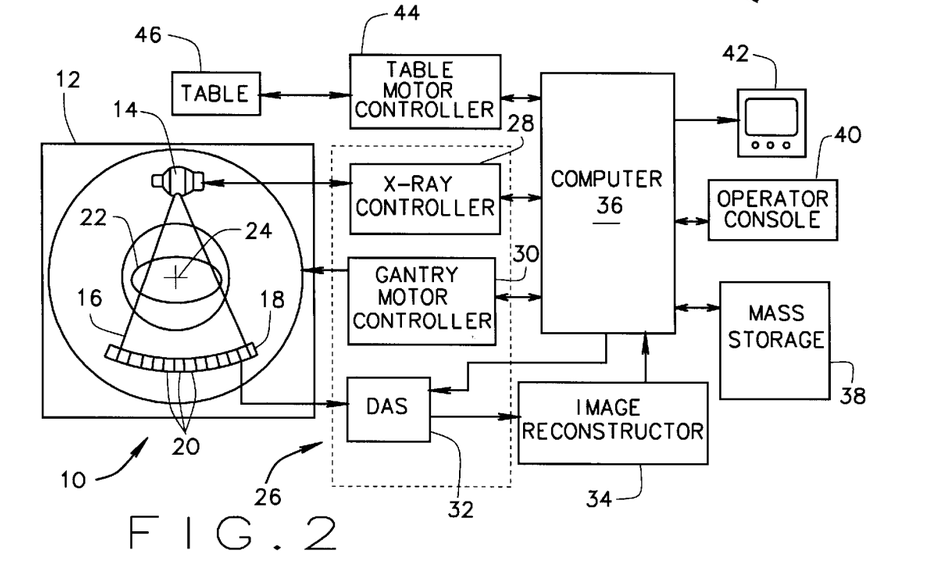
FIG. 2 is a block schematic diagram of the system illustrated in FIG. 1.

Referring to FIGS. 1 and 2, a computed tomograph (CT) imaging system 10 is shown as including a gantry 12 representative of a "third generation" CT scanner. Gantry 12 has an x-ray source 14 that projects a beam of x-rays 16 toward a detector array 18 on the opposite side of gantry 12. Detector array 18 is formed by detector elements 20 that together sense the projected x-rays that pass through an object 22, for example a medical patient. Each detector element 20 produces an electrical signal that represents the intensity of an impinging x-ray beam and hence the attenuation of the beam as it passes through patient 22. During a scan to acquire x-ray projection data, gantry 12 and the components mounted thereon rotate about a center of rotation or isocenter 24.

Rotation of gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36 that stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 that controls a motorized table 46 to position patient 22 in gantry 12. Particularly, table 46 moves portions of patient 22 through gantry opening 48.

Figure 3:
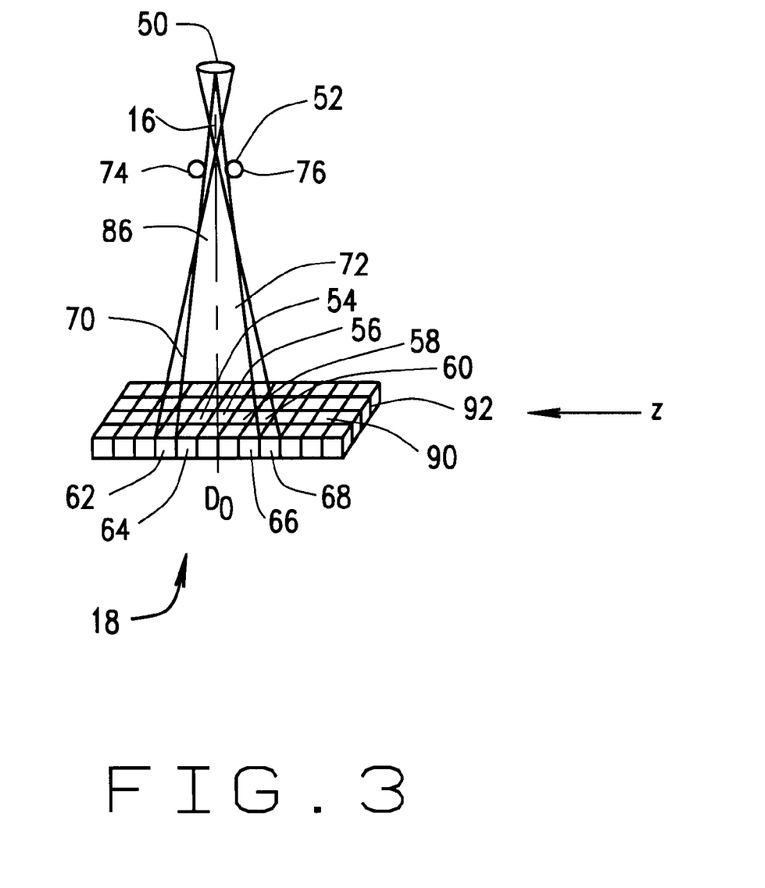
FIG. 3 is a schematic view of a portion of the CT imaging system shown in FIG. 1 showing an embodiment of a z-axis position system of the present invention.

In one embodiment, and as shown in FIG. 3, x-ray beam 16 emanates from a focal spot 50 of x-ray source 14 (FIG. 2). X-ray beam 16 is collimated by collimator 52, and collimated beam 16 is projected toward detector array 18. Detector array 18 is fabricated in a multi-slice configuration and includes detector element rows 54, 56, 58 and 60 for projection data collection. A plane 86, generally referred to as the "fan beam plane", contains the centerline of focal spot 50 and the centerline of beam 16. Fan beam plane 86 is illustrated in FIG. 3 as being aligned with a centerline $D_0$ of detector array 18, although fan beam plane 86 will not always be so aligned. Detector element rows 62, 64, 66 and 68 serve as z-position detectors for determining a z-axis position of x-ray beam 16. In one embodiment, detector rows 62, 64, 66, and 68 are rows of detector array 18. Outer rows 62 and 68 are selected to be at least substantially within penumbra 70 of beam 16. Inner rows 64 and 66 are selected to be at least substantially within umbra 72 of beam 16. "At least substantially within" means either entirely within or at least sufficiently within so that outer row 62 and 68 signal intensities depend on an x-ray beam position and inner row 64 and 66 signal intensities provide references against which outer row signals are compared. In one embodiment, collimator 52 includes tapered cams 74 and 76. (Where it is stated herein that a cam "has a taper, " it is not intended to exclude cams having a taper of zero unless otherwise stated.) X-ray controller 28 controls positioning of cams 74 and 76. Each cam can be independently positioned to alter position and width of x-ray umbra 72 relative to an edge (not shown) of detector array 18.

Figure 4:
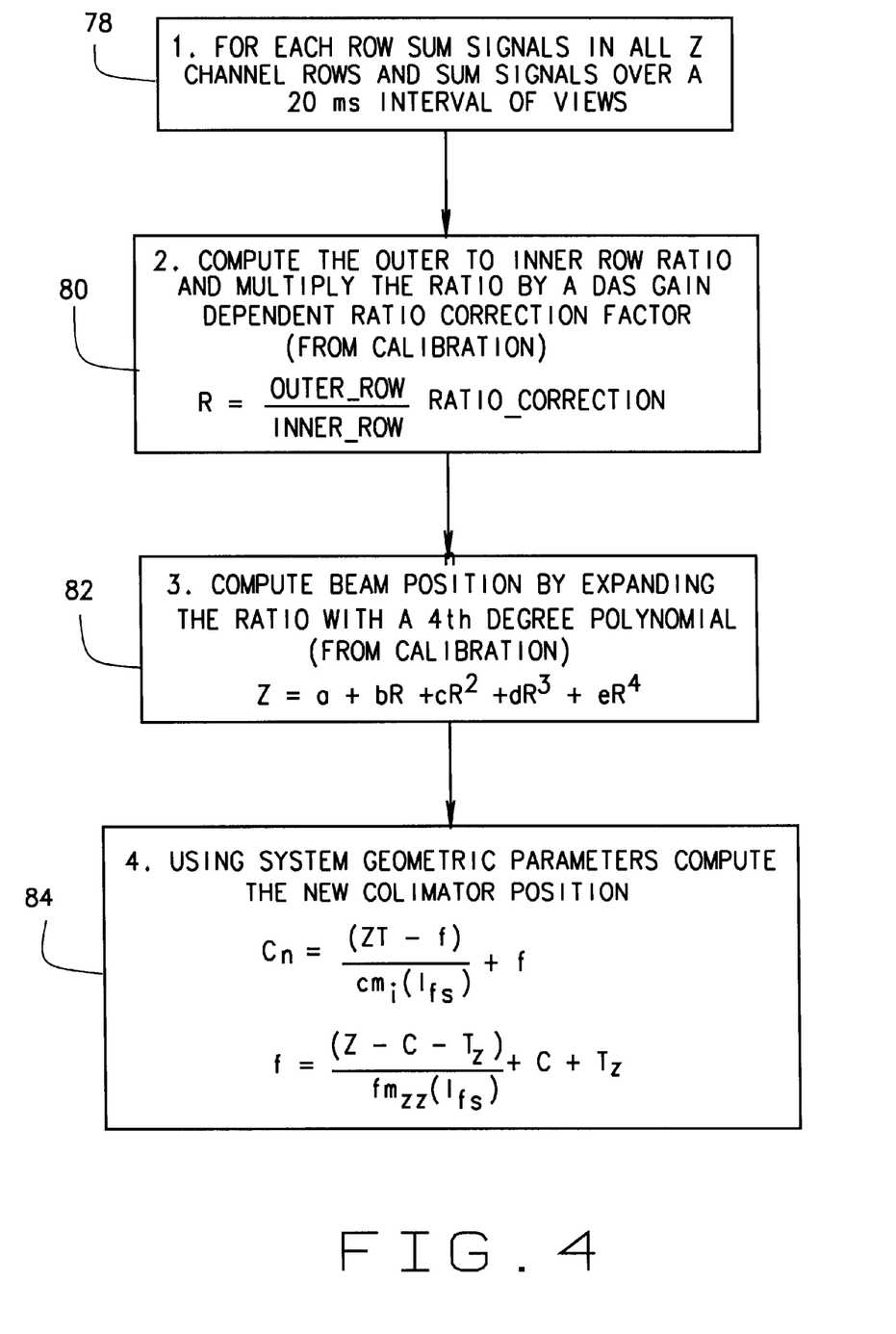
FIG. 4 is a flow diagram an embodiment of a z-axis tracking loop of the present invention.

As shown in FIG. 4, one embodiment of a closed-loop method for positioning beam 16 comprises comparing signals representation of x-ray intensity received from different rows of detector elements and positioning an x-ray beam in accordance with results of the comparison. In one embodiment, signals representative of x-ray intensity from detector rows 62, 64, 66 and 68 are summed 78 to obtain row sums. The summation is over views taken in a 20-millisecond interval. For example, after the analog signals are converted to digital format, hardware circuitry (not shown) in DAS 32 performs offset correction and determines row sums from signals received from outer row 62 and from inner row 64. A corrected ratio R is determined 80 by determining a ratio of a sum of signals received from outer row 62 to a sum of signals received from inner row 64 and multiplying the ratio by a ratio correction factor. The ratio correction factor, determined from imaging system 10 calibration, accounts for different relative DAS gains between outer row 62 and inner row 64.

Beam position Z(R) then is determined 82, in millimeters relative to a centerline. Beam position Z is obtained by applying a predetermined beam position transfer function to the corrected ratio to calculate the x-ray beam position. The beam position transfer function Z(R) is represented, for example, by a fourth-degree polynomial having predetermined coefficients:

$$Z(R) = a + bR + cR^2 + dR^3 + eR^4$$

Beam position transfer function Z(R) and its limits are specified at imaging system 10 calibration.

A new collimator position is then determined 84. A focal spot position f is determined 84 from beam position Z, current collimator position C and other system 10 geometric parameters in accordance with:

$$f = \frac{(Z - C - T_z)}{fm_{zz}(l_{fs})} + C + T_z$$

where $T_z$ represents a current taper of cam 74, $fm_{zz}$ represents a focal spot magnification factor at rows 62 and 64 and is a function of focal spot size, and $l_{fs}$ represents focal spot 50 length. A new position for collimator 52 then is determined 84 for a detector element 20 positioned toward isocenter 24. Collimator 52 is repositioned where an edge (not shown) of collimator 52 would meet a line between focal spot position f and a target beam position $Z_t$ which has been specified at imaging system 10 calibration. New collimator position $C_n$ thus is determined in accordance with:

$$C_n = \frac{(Z_t - f)}{cm_i(l_{fs})} + f$$

where $cm_i$ represents a current collimator magnification factor at detector element 20 positioned toward isocenter 24 and is a function of focal spot size, and $l_{fs}$ represents focal spot 50 length.

In one embodiment, steps 78, 80, 82, and 84 are performed independently for each side of collimator 52 at intervals to continuously obtain new positions for each side of collimator 52. These intervals are, in one embodiment, 20 milliseconds, to sample the x-ray beam 16 position 25 times during a 0.5 second scan to minimize control loop lag error. However, in other embodiments, the interval is between 5 milliseconds and 50 milliseconds. In still other embodiments, the interval is between a minimum value sufficient to avoid effects of quantum noise and high frequency variation (such as due to x-ray tube anode movement at a run frequency between 50 Hz and 160 Hz) and a maximum constrained by a slew rate of the sag curve. Sampling the changing sag curve frequently avoids excessive positioning error. (Sag is a periodic movement of x-ray beam 16 resulting from gravity and from centrifugal forces acting on mechanical structure during a rotation of gantry 12.)

During patient scanning, z-position detectors 62, 64, 66 or 68 may become blocked by patient clothing, blankets, or other object. After blockage of a z-position detector 62, 64, 66, or 68 has been detected, or when x-ray source 14 first turns on, the loop sample interval is adjusted downward. In one embodiment, the loop sample interval is adjusted downward to 5 milliseconds. After 4 milliseconds of stabilization, the position of the beam is measured and collimator positioning is started to further minimize initial position errors.

During a blockage, loop operation is suspended. To determine if any z-position detectors are blocked, a signal from a last data detector element 90 adjacent a z-position detector 62, 64, 66 or 68 is compared to an expected signal Sx. Z-position detector blockage is assumed, in one embodiment, if a last data letector element 20 signal is less than 0.9 times expected signal Sx. In other embodiments, detector blockage is assumed when a last data detector element 20 signal is less than a value between 0.95 and 0.5 times expected signal Sx. (It is desirable to make this value as large in magnitude as possible to identify patient blockage as quickly as possible, thereby avoiding mispositioning of x-ray beam 16 due to corrupted Z-measurement data. A maximum of 0.95 is used in one embodiment because it is known that x-ray scatter blockage from large patients 22, for example, can reduce a signal to 0.95 times the expected value.) During a blockage, collimator positioning is suspended. However, position measurement continues at an interval that is decreased from 20 to 5 milliseconds. The decreased measurement interval allows imaging system 10 to more quickly detect an end of the blockage and to resume closed-loop positioning.

Expected signal Sx is written as:

$$Sx = gmA * csf * t * g,$$

where gmA is a generator current mA signal proportional to an x-ray source 14 energizing current, csf is a scale factor determined at system 10 calibration, t is a DAS sample time period, and g is a gain factor. Gain factor g allows expected signal Sx to be adjusted according to a gain value used for scanning. In one embodiment, this gain value is selectable from a plurality of gain values available in system 10.

In one embodiment, closed loop tracking is suspended when signal corruption is detected. Signal corruption is detected, for example, by determining an actual focal spot length from a beam position and a collimator position, and comparing the actual focal spot length to a nominal focal spot length. When a difference of, for example, more than 0.1 millimeter is detected between the actual focal spot length and the nominal spot length, corruption is assumed to exist and collimator positioning is suspended. (In other embodiments, a difference threshold for assuming corruption is as small as 0.05 millimeter or as large as about 0.6 millimeter. In still other embodiments, a value is selected between a lower limit set by higher probabilities of false activation due to noise, x-ray scatter and/or momentary beam position disturbances and an upper limit that still provides some of the advantages of tracking.) However, beam position measurement continues at a decreased interval, as when a blockage is detected. Such corruption may occur, for example, for a short time just prior to or just following detection of a patient blockage. If the corruption persists, for example, over 90° of rotation of gantry 12 without detecting a patient blockage, a malfunction of the tracking system requiring servicing has likely occurred. In such an event, a scan is immediately aborted to avoid patient dose and collection of non-diagnostic quality images. In other embodiments, a limit is set from as little as 45° to as much as 360° of a rotation of gantry 12. In other embodiments, a limit is set between a value at which a false alarm rate due to scatter and/or an occasional exceptionally long partial patient 22 blockage is acceptable and an upper limit representing a design choice as to how long compromised operation (high dose and/or non-diagnostic quality images) can be tolerated before terminating a scan.

After system 10 has been switched off, position of focal spot 50 changes as source 14 cools over time. In one embodiment, before system 10 is switched on again, an initial focal spot position is approximated from information obtained when a focal spot position was last measured. An approximation of a linear function is used to model focal spot position change during cooling in one embodiment, and in another embodiment, the linear function is a 97 nanometer per second linear function. Because position change with cooling is an exponential function, the linear approximation is clamped at 0.15 millimeters. This clamping corresponds to approximately 20% of a cooling change in system 10 when fully cold, where a linear approximation to the exponential function suffices. A fully cold position requires 8 to 12 hours without patient scanning, and a tube warm up prior to patient scanning is normally requested if the tube has been off more than 1 hour. Therefore, a fully cold position, although possible, is not likely during normal patient scanning. During tube warm up a current measured position of the focal spot is established again for initial positioning of the collimator.

Figure 5:
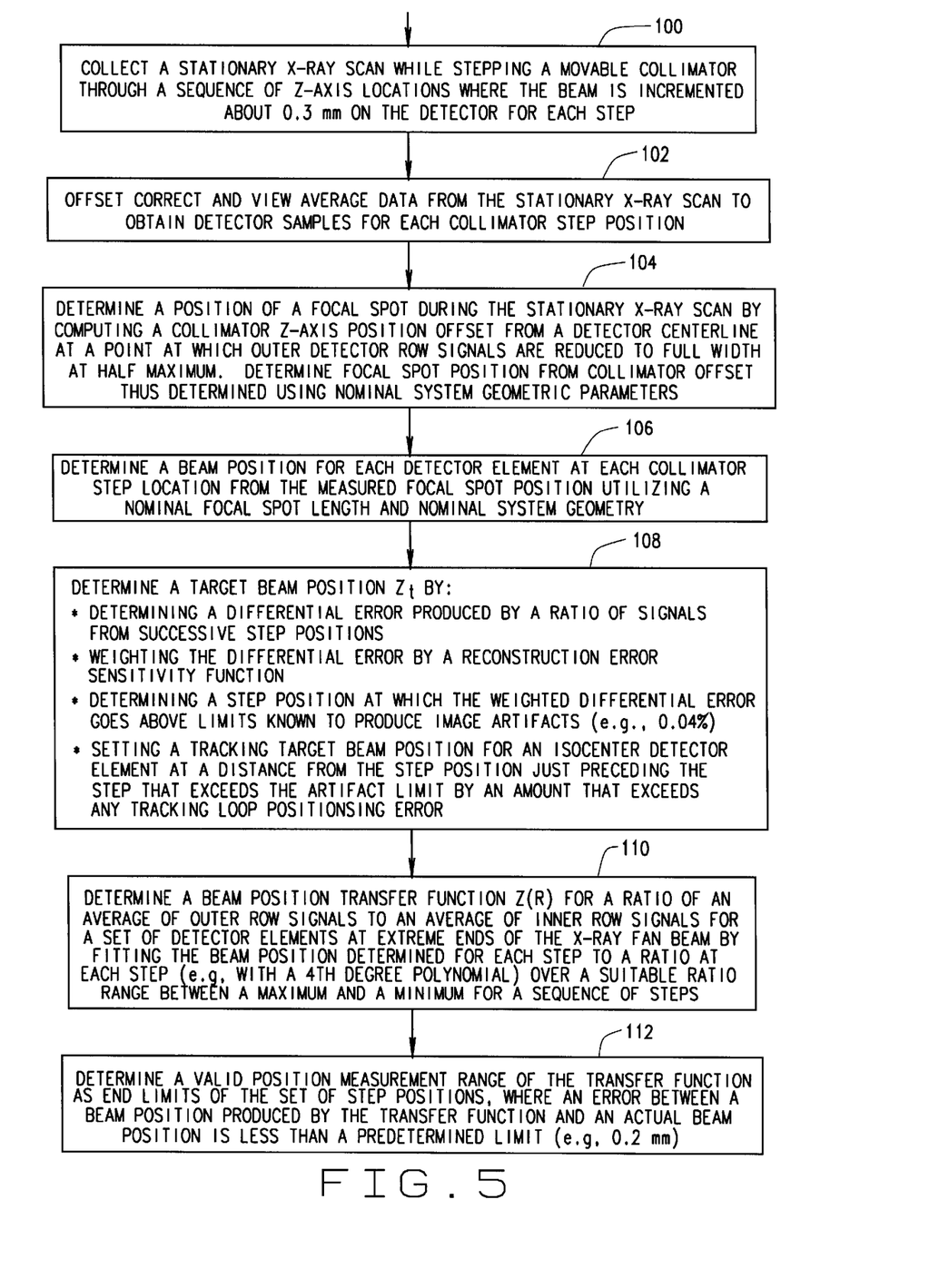
FIG. 5 is a flow diagram of a method for calibrating tracking loop parameters.

Several tracking loop parameters described herein, specifically, beam position transfer function Z(R) and its limits and target beam position $Z_t$, are determined at system 10 calibration. FIG. 5 illustrates one embodiment of a method for calibrating tracking loop parameters. In this embodiment, data from a stationary sweep scan is collected 100 while collimator 52 is stepped through a sequence of z-axis positions. Beam 16 is incremented 0.3 millimeters on detector array 18 exposure surface for each collimator 52 step position. The sweep scan data is offset-corrected and view averaged 102 to obtain a set of detector samples for each collimator 52 step position. A position of the focal spot is then determined 104. A collimator 52 z-axis position offset from detector array centerline Do is determined 104, as the point where outer rows 62 and 68 receive signals of half-maximum intensity at full detector element 20 width. Position of focal spot 50 during sweep scan then is determined 104 from collimator 52 z-axis offset and nominal system 10 geometric parameters.

A beam 16 position is determined 106 for each detector element 20 at each collimator 52 step position. Beam 16 positions are determined from sweep scan focal spot 50 position, nominal length of focal spot 50, and nominal system 10 geometry.

Target beam position $Z_t$ then is determined 108 for detector element 20 positioned toward isocenter 24. When beam 16 is directed at target beam position $Z_t$, beam 16 is sufficiently close to detector array 18 edge 92 to prevent imaging artifacts but is far enough away to minimize patient dosage. To determine target beam position $Z_t$, ratios of detector samples for successive collimator 52 step positions are utilized to determine a detector differential error. A reconstruction error sensitivity function w(i) then is applied to weight the detector differential error. Reconstruction error sensitivity function w(i) is related to the percent positive contribution of a detector element 20 as a function of its radial distance from isocenter 24. Function w(i), in one embodiment, is computed from nominal system geometry. In another embodiment, w(i) is empirically determined. For example, the following equations describe an empirical determination of w(i):

$$b(i) = .018, \qquad 0 \le i \le 5$$

$$b(i) = .035 + .00075 \times (i - 5), \qquad 5 \le i \le 213$$

$$b(i) = .414 + .00365 \times (i - 213), \qquad 214 \le i \le n$$

where i represents detector element position from isocenter 24 and b(i) represents an artifact threshold, i.e. a percent differential error, for a double detector element 20 error. Reconstruction error sensitivity function w(i) then is determined in accordance with:

$$w(i) = 0.18/b(i).$$

A collimator 52 step position SP is determined for which the weighted detector differential error exceeds a limit L empirically known to produce image artifacts, for example, 0.04 percent. Target beam position $Z_t$ then is set for the isocenter detector element at a distance just preceding SP by an amount exceeding applicable tracking loop positioning error.

Beam position transfer function Z(R) then is determined 110 for a ratio R of an average of outer row 62 to inner row 64 signals for a set of detector elements at an extreme end of x-ray fan beam 16. Beam 16 positions, determined 106 for each collimator 52 step position, are fitted to the ratio for each collimator 52 step position with a fourth-degree polynomial, for example, in accordance with.

$$Z(R)=a+bR+cR^2+dR^3+eR^4$$

over a suitable ratio range between a maximum and minimum for the sequence of steps.

A valid position measurement range for Z(R) is determined 112 as between end limits of the set of collimator 52 step positions for which an error between a beam 16 position determined by Z and an actual beam 16 position is less than a predetermined limit, for example, 0.2 millimeters. In other embodiments, the predetermined limit is between 0.1 millimeters to 0.6 millimeters. In still other embodiments, the predetermined limit is set at a value between a lower limit just above a value at which a range of beam 16 position that can be precisely measured is too limited, and just below a lower limit that is deemed to create tracking errors so large as to unacceptably compromise the benefits of tracking.

The above-described tracking loop senses the signal ratio between detector rows and moves system collimation to maintain the x-ray beam very close to the imaging system detector array edge during patient scanning. As a result, patient x-ray dosage is reduced 20 to 40 percent without sacrificing image quality.

Other functions can be utilized in place of beam position transfer function Z(R) and also in place of reconstruction error sensitivity function w(i).

In some embodiments, the methods described herein are implemented by software, firmware, or by a combination thereof controlling either computer 36, image reconstructor 34, or both. Also, additional z-detector rows can be provided. In such an embodiment, various combinations of z-detector row signals can be used as the inner and outer row signals, thereby becoming identified as such, or a different and/or more elaborate transfer function can be used to determine a beam position.

The above described calibration methods and apparatus provides improved calibration for z-axis tracking loops for positioning x-ray beams on multi-slice detectors of CT imaging systems. The methods and apparatus provide a target beam position at which to maintain the x-ray beam, a transfer function to convert detector ratio information into a beam position in millimeters (or other suitable units via conversion factors), and valid limits of the ratio to beam position transfer function.

It should be understood that system 10 is described herein by way of example only, and the invention can be practiced in connection with other types of imaging systems. Furthermore, it will be recognized by those skilled in the art that the calibration system described herein is also useful for other applications which require x-ray beam tracking calibration, such as for object location or sensing of movement.

While the invention has been described in terms of various specific embodiments, those skilled in the art will recognize that the invention can be practiced with modification within the spirit and scope of the claims.

What is claimed is:

1. A method for determining tracking control parameters for positioning an x-ray beam of a computed tomography imaging system, the imaging system including a movable collimator positionable in steps and a detector array including a plurality of rows of detector elements, said method comprising the steps of:
    obtaining detector samples at a plurality of collimator step positions while determining a position of a focal spot of the x-ray beam;
    determining a beam position for each detector element at each collimator step utilizing the determined focal spot positions, a nominal focal spot length, and geometric parameters of the x-ray beam, collimator, and detector array;
    determining a detector element differential error according to ratios of successive collimator step positions; and
    selecting a target beam position for an isocenter element in accordance with the determined element differential errors.

2. A method in accordance with claim 1 wherein the plurality of detector rows are z-axis detector rows, and the detector array has a centerline perpendicular to the z-axis, an outer detector row, and an inner detector row: said determining a position of a focal spot of the x-ray beam comprises the steps of:
    determining a collimator z-axis position offset from the detector array centerline at a point at which outer detector row signals are reduced to a full width at a half maximum; and
    determining a focal spot position as a function of the determined collimator z-axis position and the geometric parameters of the x-ray beam, collimator, and detector array.

3. A method in accordance with claim 1 further comprising the step of offset-correcting and view-averaging the obtained detector samples at a plurality of collimator step positions to obtain a set of detector samples for each collimator step position used in said step of determining a beam position and said step of determining a differential error for selection of the target beam position.

4. A method in accordance with claim 1 wherein selecting a target beam position for an isocenter detector element in accordance with the determined element differential errors comprises the steps of:
    weighting the detector element differential error by a reconstruction error sensitivity function;
    determining a step position at which the weighted detector element differential error exceeds a predetermined limit; and
    setting a tracking beam position for the isocenter detector element at a distance from the determined step position preceding a step that exceeds a predetermined artifact limit by an amount that exceeds a tracking loop positioning error.

5. A method in accordance with claim 4 wherein the reconstruction error sensitivity function is detector element dependent.

6. A method in accordance with claim 5 wherein the reconstruction error sensitivity varies according to a distance of the detector element from an isocenter element.

7. A method in accordance with claim 4 wherein the detector rows have at least 214 elements on each side of an isochannel element, and the reconstruction error sensitivity function is:

$$w(i)=0.18/b(i);$$

where: i=a detector element position from an isocenter detector element;
    b(i)=an artifact threshold (% differential error) for a double detector element error; and $$b(i) = .018, \qquad 0 \le i \le 5$$

$$b(i) = .035 + .00075 \times (i-5), \qquad 5 \le i \le 213$$

$$b(i) = .414 + .00365 \times (i-213), \qquad 214 \le i \le n.$$

8. A method for determining tracking control parameters for positioning an x-ray fan beam of a computed tomography imaging system, the imaging system including a movable collimator positionable in steps and a detector array including a plurality of rows of detector elements including at least an inner row and an outer row, said method comprising the steps of:
obtaining detector samples at a plurality of collimator step positions while determining a position of a focal spot of the x-ray fan beam;
determining a beam position for each detector element at each collimator step utilizing the determined focal spot positions, a nominal focal spot length, and geometric parameters of the x-ray fan beam, collimator, and detector array; and
determining a beam position transfer function for a ratio of an average of detector outer row signals to detector inner row signals for a set of detector elements at an extreme end of the x-ray fan beam in accordance with a selected approximation over a selected ratio range between a minimum and a maximum ratio for the plurality of collimator step positions.

9. A method in accordance with claim 8 wherein determining a beam position transfer function comprises the steps of fitting, to a polynomial function, the determined beam positions at each step as a function of the ratio of an average of detector outer row signals to detector inner row signals.

10. A method in accordance with claim 9 wherein the polynomial function is a fourth degree polynomial.

11. A method in accordance with claim 8 further comprising the step of determining a valid measurement range of the transfer function as end limits of the plurality of collimator step positions for which an error between beam positions computed using the transfer function and an actual beam position is less than a predetermined limit.

12. A method in accordance with claim 11 wherein the predetermined limit is between 0.1 millimeters and 0.6 mm.

13. A method in accordance with claim 11 wherein the predetermined limit is 0.2 millimeters.

14. A computed tomography imaging system comprising an x-ray source, a detector array including a plurality of rows of detector elements, and a movable collimator positionable in steps and configured to collimate and position an x-ray beam produced by said x-ray source on said detector array, said system configured to:
obtain detector samples at a plurality of collimator step positions while determining a position of a focal spot of the x-ray beam;
determine a beam position for each detector element at each collimator step utilizing the determined focal spot positions, a nominal focal spot length, and geometric parameters of the x-ray beam, collimator, and detector array;
determine a detector element differential error according to ratios of successive collimator step positions; and
select a target beam position for an isocenter element in accordance with the determined element differential errors.

15. A system in accordance with claim 14 wherein the plurality of detector rows are z-axis detector rows, and the detector array has a centerline perpendicular to the z-axis, an outer detector row, and an inner detector row; and said system being configured to determine a position of a focal spot of the x-ray beam comprises said system being configured to:
determine a collimator z-axis position offset from the detector array centerline at a point at which outer detector row signals are reduced to a full width at a half maximum; and
determine a focal spot position as a function of the determined collimator z-axis position and the geometric parameters of the x-ray beam, collimator, and detector array.

16. A system in accordance with claim 14 further configured to offset-correct and view-average the obtained detector samples at a plurality of collimator step positions to obtain a set of detector samples for each collimator step position used in determining said beam position and in determining said differential error for selection of said target beam position.

17. A system in accordance with claim 14 wherein said system being configured to select a target beam position for an isocenter detector element in accordance with the determined element differential errors comprises said system being configured to:
weight the detector element differential error by a reconstruction error sensitivity function;
determine a step position at which the weighted detector element differential error exceeds a predetermined limit; and
set a tracking beam position for the isocenter detector element at a distance from the determined step position preceding a step that exceeds a predetermined artifact limit by an amount that exceeds a tracking loop positioning error.

18. A system in accordance with claim 17 wherein the reconstruction error sensitivity function is detector element dependent.

19. A system in accordance with claim 18 wherein the reconstruction error sensitivity varies according to a distance of the detector element from an isocenter element.

20. A system in accordance with claim 17 wherein the detector rows have at least 214 elements on each side of an isochannel element, and the reconstruction error sensitivity function is:

$$w(i)=0.18/b(i);$$

where: i=a detector element position from an isocenter detector element;
b(i)=an artifact threshold (% differential error) for a double detector element error; and $$b(i) = .018, \qquad 0 \le i \le 5$$

$$b(i) = .035 + .00075 \times (i-5), \qquad 5 \le i \le 213$$

$$b(i) = .414 + .00365 \times (i-213), \qquad 214 \le i \le n.$$

21. A computed tomography imaging system comprising an x-ray source, a detector array including a plurality of rows of detector elements, and a movable collimator positionable in steps and configured to collimate and position an x-ray beam produced by said x-ray source on said detector array, said system configured to:
obtain detector samples at a plurality of collimator step positions while determining a position of a focal spot of the x-ray fan beam;

determine a beam position for each detector element at each collimator step utilizing the determined focal spot positions, a nominal focal spot length, and geometric parameters of the x-ray fan beam, collimator, and detector array; and determine a beam position transfer function for a ratio of an average of detector outer row signals to detector inner row signals for a set of detector elements at an extreme end of the x-ray fan beam in accordance with a selected approximation over a selected ratio range between a minimum and a maximum ratio for the plurality of collimator step positions.

22. A system in accordance with claim 21 wherein said system being configured to determine a beam position transfer function comprises the steps of fitting, to a polynomial function, the determined beam positions at each step as a function of the ratio of an average of detector outer row signals to detector inner row signals.

23. A system in accordance with claim 22 wherein the polynomial function is a fourth degree polynomial.

24. A system in accordance with claim 21 further configured to determine a valid measurement range of the transfer function as end limits of the plurality of collimator step positions for which an error between beam positions computed using the transfer function and an actual beam position is less than a predetermined limit.

25. A system in accordance with claim 24 in which the predetermined limit is between 0.1 and 0.6 millimeters.

26. A system in accordance with claim 24 in which the predetermined limit is 0.2 millimeters.

* * * * *